United States Patent [19]

Lazarus

[11] 4,175,122

[45] Nov. 20, 1979

[54] BIOLOGICALLY ACTIVE AMIDES

[75] Inventor: Norman R. Lazarus, Gravesend, England

[73] Assignee: Burroughs Wellcome Co., Research Triangle Park, N.C.

[21] Appl. No.: 851,706

[22] Filed: Nov. 15, 1977

Related U.S. Application Data

[63] Continuation-in-part of Ser. No. 676,645, Apr. 14, 1976, abandoned.

[30] Foreign Application Priority Data

Apr. 15, 1975 [GB] United Kingdom ............... 15414/75
Mar. 31, 1976 [GB] United Kingdom ............... 12945/76

[51] Int. Cl.² ...................... A61K 37/02; A61K 37/24
[52] U.S. Cl. .................................................. 424/177
[58] Field of Search ............................................ 424/177

[56] References Cited

U.S. PATENT DOCUMENTS 3,676,551  7/1972  Thiullier ................................ 424/177
3,868,356  2/1975  Smyth ................................... 424/177
3,868,357  2/1975  Smyth ................................... 424/177

FOREIGN PATENT DOCUMENTS 1951M   4/1962  France ...................................... 424/177
2123524  8/1972  France ...................................... 424/177
1407807 10/1972 France ...................................... 424/177
2204409  5/1974  France ...................................... 424/177
351565   3/1961  Switzerland .............................. 424/177

*Primary Examiner*—Delbert R. Phillips
*Attorney, Agent, or Firm*—Donald Brown

[57] ABSTRACT

A polypeptide, designated Pancreatic Hormone III, together with pharmaceutically acceptable salts or metal complexes thereof; pharmaceutical formulations of the said polypeptide or its salts or complexes and the preparation of such formulations; and the use of the said polypeptide, salts and complexes in human and veterinary medicine in effecting a reduction in weight or in appetite or in the treatment of obesity, hyperglycaemia or hyperinsulinaemia.

9 Claims, No Drawings

BIOLOGICALLY ACTIVE AMIDES

PRIOR APPLICATION

This application is a continuation-in-part of Ser. No. 676,645 filed Apr. 14, 1976.

This invention relates to biologically active polypeptides isolatable from the pancreas of vertebrate species, to pharmaceutical formulations containing these polypeptides and the preparation of such formulations, and to the use of the polypeptides in human and veterinary medicine.

It is known from the literature (for example, *Endocrinology* 83, 1323 (1968) and 93, 558 (1973), and *J. Biol. Chem.*, 250/24, 9369 (1974)) that by means of acid-alcohol extraction procedures a polypeptide can be isolated from the pancreas of a number of avian and mammalian species which is structurally and pharmacologically distinguishable from the known pancreatic hormones insulin, somatostatin and glucagon. Immunological and other studies have further indicated that the polypeptide varies in structure with the species of origin.

The amino acid sequences of the bovine pancreatic polypeptide (BPP) and avian pancreatic polypeptide (APP, from chicken) to which inter alia this invention relates are set out in *Gastroenterology*, 47/4, 737 (1974). The polypeptides are identified as straight-chain sequences of thirty-six amino acid residues having identities at fifteen positions. Similar polypeptides have been isolated from the pancreas of pig (PPP), sheep (OPP) and man (HPP) and are taught (*Gastroenterology*, loc. cit.) as differing structurally from BPP in only one or two residues at positions 2,6 or 23. (All references recited herein are incorporated herein by reference thereto).

Of these pancreatic polypeptides APP and BPP in particular have been extensively investigated as regards biological activity and as recently as 1974 it was stated (*Gastroenterology*, loc. cit.) that the physiological role of BPP and APP was unknown.

It has now unexpectedly been found by the Applicants that these vertebrate pancreatic polypeptides (hereinafter collectively referred to as VPPs, which term should be understood to include such polypeptides of avian, amphibian, piscian, reptilian or mammalian origin) are as a class effective in lowering the concentration in the blood of both glucose and insulin when administered to a strain (NZO) of genetically obese, hyperglycaemic and hyperinsulinaemic mice. At the same time these treated mice lose weight as compared with untreated control animals and give normalized values in the oral Glucose Tolerance Test standard in the art. It has also been found that these VPPs are as a class effective in reducing the food consumption of obese rats of the Zucker strain as compared with obese untreated control animals and that when compared with such controls the obese VPP-treated animals lose weight.

In consequence of their newly-found activities as above described the VPPs may be used in the treatment of mammals in the fields of both human and veterinary medicine for the amelioration of a condition characterised by one of more of obesity, hyperglycaemia and hyperinsulinaemia. Thus specific utilities for the VPPs include treatment of the following conditions:

(a) obesity associated with normal blood levels of both glucose and insulin;

(b) obesity associated with hyperinsulinaemia but normal blood glucose levels;

(c) obesity associated with both hyperinsulinaemia and hyperglycaemia, as for example in lateonset (middle-aged) diabetes in man; and (d) the need or desire to reduce the appetite for food or induce loss of weight.

In the veterinary field a particularly important application is in the treatment of domestic pet animals, particularly cats and dogs.

For each of these utilities the amount required of VPP and the frequency of its administration will vary with the identity of the VPP concerned and with the nature and severity of the condition being treated and is of course ultimately at the discretion of the physician or veterinarian. In general however a suitable dose of VPP will lie in the range of 0.01 to 100 $\mu$g per kilogram mammal body weight being treated, preferably in the range of 0.02 to 20 $\mu$g per kilogram and most preferably in the range 0.02 to 4.0 $\mu$g per kilogram. Administration by the parenteral route (intravenously, intradermally, intramuscularly or subcutaneously) is preferred.

While it is possible for the VPPs to be administered as the raw substances it is preferable, in view of their potency, to present them as a pharmaceutical formulation. The formulations, both veterinary and for human use, of the present invention comprise a VIP together with one or more acceptable carriers therefor and optionally other therapeutic ingredients. The carrier(s) must be "acceptable" in the sence of being compatible with the other ingredients of the formulation and not deleterious to the recipient thereof. Desirably the formulations should not include oxidising agents and other substances with which peptides are known to be incompatible. The formulations may conveniently be presented in unit dosage form and may be prepared by any of the methods well known in the art of pharmacy. All methods include the step of bringing into association the VPP with the carrier which constitutes one or more accessory ingredients. In general the formulations are prepared by uniformly and intimately bringing into association the VPP with the carrier(s) and then, if necessary, dividing the product into unit dosages thereof.

Formulations suitable for parenteral administration conveniently comprise sterile aqueous preparations of the VPPs which are preferably isotonic with the blood of the recipient. Such formulations may be conveniently prepared by admixing solid VPP with water to produce a solution or suspension which is filled into a sterile container and sealed against bacterial contamination. Preferably sterile materials are used under aseptic manufacturing conditions to avoid the need for terminal sterilisation.

Such formulations may optionally contain one or more additional ingredients among which may be mentioned preservatives, such as methyl hydroxybenzoate, chlorocresol, metacresol, phenol and benzalkonium chloride. Such materials are of especial value when the formulations are presented in multi-dose containers.

Buffers may also be included to provide a suitable pH value for the formulation and suitable materials include sodium phosphate and acetate. Sodium chloride or glycerin may be used to render a formulation isotonic with the blood. If desired the formulations may be filled into the containers under an inert atmosphere such as nitrogen or may contain an antioxidant, and are conveniently presented in unit dose or multidose form, for example in a sealed ampoule.

Where a formulation is presented for human or for veterinary use, then each dosage unit thereof conveniently contains the VPP in an amount in the range of 0.5 µg to 5.0 mg, preferably 1.0 µg to 1.0 mg and more preferably 1.0 µg to 200 µg.

| | |
|---|---|
| BPP | Ala.Pro.Leu.Glu.Pro.Gln.Tyr.Pro.Gly.Asp.Asp.Ala. |
| APP | Gly.Pro.Ser.Gln.Pro.Thr.Tyr.Pro.Gly.Asp.Asp.Ala. |
| | 1              6              12 |
| BPP | Thr.Pro.Glu.Gln.Met.Ala.Gln.Tyr.Ala.Ala.Glu.Leu. |
| App | Pro.Val.Glu.Asp.Leu.Ile.Arg.Phe.Tyr.Asp.Asn.Leu. |
| | 13              18              24 |
| BPP | Arg.Arg.Tyr.Ile.Asn.Met.Leu.Thr.Arg.Pro.Arg.TyrNH$_2$ |
| APP | Gln.Gln.Tyr.Leu.Asn.Val.Val.Thr.Arg.His.Arg.TyrNH$_2$ |
| | 25              30              36 |

It should be understood that excluded from the scope of the present invention are non-sterile mixtures which are mere solutions or suspensions of the known VPPs in solvents and liquids known in the literature for use in their synthesis and/or isolation by the methods described therein. Included within the scope of the present invention are such solutions and suspensions of the known substances which are pharmaceutically acceptable to the intended recipient thereof and which contain in addition at least one other pharmaceutically acceptable substance.

It will be appreciated that while VPPs form acid addition salts and carboxy acid salts the biological activity thereof will reside in the base/acid (polypeptide) therein. These salts may be used in human and in veterinary medicine and presented as pharmaceutical formulations in the manner and in the amounts (calculated as the base) described hereinabove, and it is then preferable that the acid moiety be pharmacologically and pharmaceutically acceptable to the recipient. Examples of such suitable acids include (a) mineral acids: hydrochloric, hydrobromic, phosphoric, metaphosphoric, nitric and sulphuric acids; (b) organic acids: tartaric, acetic, citric, malic, lactic, fumaric, benzoic, glycollic, gluconic, gulonic, succinic and aryl-sulphonic, for example p-toluenesulphonic acids.

The pharmaceutically and pharmacologically acceptable salts together with those salts which are not so acceptable (for example salts of hydrofluoric and perchloric acids) have utility in isolation and purification of the VPPs, and of course the unacceptable salts are also valuable in the preparation of the acceptable salts by techniques well known in the art. Those VPPs containing a plurality of free amino groups may be obtained in the form of mono- or poly- acid addition salts, or as mixed salts of a plurality of acids.

Those VPPs, such as APP (vid. sup.), which include a histidyl radical form complexes with pharmaceutically acceptable metals such as zinc, and such complexes have been found to exhibit a prolonged period of action upon parenteral administration as compared with the un-complexed polypeptides and their acid addition salts. Such complexes may be prepared by techniques analogous to those well known in the art in respect of insulin and may be used in human and in veterinary medicine, and presented as pharmaceutical formulations, in the manner and in the amounts (calculated as the polypeptide) described hereinabove. The formation of zinc-insulin complexes is taught in, for example, *Acta Chemica Scandinavica*, 10 (1956) 1455 and 1459, and 11 (1957) 291, 299, 439, 484 and 1248.

In the *Journal of Biological Chemistry*, 250/24, p.p. 9369–9376 (1975), Kimmel, J. R. et al., suggest that the name "pancreatic hormone III" or the abbreviated version "PH-III" may be used to refer to the polypeptides referred to herein, and assign to BPP and APP the following structures:

Published United Kingdom Patent Specification No. 1,373,310, U.S. Pat. No. 3,842,063 and Swiss Pat. No. 551, 949 (each of which is incorporated herein by reference hereto) teach inter alia structures for VPP's (Pancreatic Hormone III) of respectively bovine, porcine, ovine and human origin, together with the extraction and isolation of the polypeptides from pancreas and their characterization. VPP's of known structure may be synthesised by classical peptide synthetic methods and VPP's of other species may be isolated from pancreas by procedures analogous to those taught in the patent specifications and other literature incorporated herein by reference. Such procedures are themselves analogous to classical extraction procedures used for the separation of insulin and typically include an initial acid/alcohol extraction of the pancreatic material, removal of lipid, concentration, and fractional separation of the insulin, glucagon and VPP (Pancreatic Hormone III) by one of more of a variety of methods including gel filtration, ion exchange chromatography, electrophoresis and countercurrent distribution.

It will be appreciated from the foregoing that what we will claim may comprise any novel feature described herein, principally and not exclusively, for example:

(a) A pharmaceutical formulation which comprises a polypeptide designated Pancreatic Hormone III or a pharmaceutically acceptable salt or metal complex of said polypeptide, together with a pharmaceutically acceptable carrier therefor.

(b) A sterile parenterally acceptable pharmaceutical formulation which comprises a polypeptide, or a salt or complex thereof as defined in (a) above together with a pharmaceutically acceptable carrier therefor.

(c) A formulation as defined in (a) or (b) above wherein the polypeptide is isolatable from a mammalian species, for example ox, sheep or pig.

(d) A method of preparing a pharmaceutical formulation as defined in (a), (b) or (c) above which comprises admixture of the polypeptide, or a salt or complex thereof with the carrier therefor and, where appropriate, sterilization and/or division of the product into unit dosages thereof.

(e) A method for treating a mammal for a condition selected from obesity, hyperglycaemia and hyperinsulinaemia which comprises the administration to the mammal of a non-toxic, obesity reducing, hyperglycaemic or hyperinsulinaemic treatment effective amount respectively of a polypeptide, or a salt or complex thereof as defined in (a) or (c) above.

(f) A method of reducing the weight or reducing the appetite of a mammal comprising the administration to the mammal of a non-toxic weight-reducing or appetite-reducing treatment effective amount respectively of a polypeptide, or a salt or complex thereof as defined in (a) or (c) above.

(g) A method as defined in (e) or (f) above wherein the mammal treated is man.

The following examples illustrate the present invention but should not be construed as in any way constituting a limitation thereof.

In each of the following examples the APP and BPP, as appropriate, were respectively the avian pancreatic polypeptide and bovine pancreatic polypeptide referred to in the foregoing description.

EXAMPLE 1

Injection of APP 5.0 μg/ml

| APP | 0.5mg |
| --- | --- |
| Dilute Acetic Acid | sufficient to produce pH 4.0 |
| Water for Injections B.P. | to 100.0ml |

The APP was dissolved in 9/10 of the final volume of Water for Injections adjusted to pH 4.0 with dilute Acetic Acid. The solution was diluted to volume with the remaining Water and sterilised by passage through a membrane filter, 0.22 μm pore size. The sterile solution was distributed aseptically into 1 ml. ampoules which were sealed by fusion of the glass.

An analogous formulation was prepared wherein the APP was replaced by BPP.

EXAMPLE 2

Multidose Injection of APP 50 μg/ml

| APP | 5.0mg |
| --- | --- |
| Sodium Phosphate Hydrated B.P. | 0.85g |
| Dilute Phosphoric Acid | sufficient to produce pH 7.0 |
| Methyl Hydroxybenzoate | 0.12g |
| Water for Injections B.P. | to 100.0ml |

The Methyl Hydroxybenzoate was dissolved in 9/10 of the final volume of Water at 85° C. The solution was cooled to below 25° C. and the Sodium Phosphate added followed by sufficient Phosphoric Acid to produce pH 7.0. The APP was then added and dissolved and the solution diluted to volume with Water. After sterilisation by passage through a membrane filter, 0.22 μm pore size, the solution was distributed aseptically into 10 ml glass vials which were sealed with rubber stoppers secured by an aluminum collar.

An analogous formulation was prepared wherein the APP was replaced by BPP.

EXAMPLE 3

Isotonic multidose injection of APP 5 μg/ml

| APP | 0.50mg |
| --- | --- |
| Chlorocresol | 0.10g |
| Sodium Chloride | 0.86g |
| Water for Injections B.P. | to 100.00ml |

The Chlorocresol was dissolved in 9/10 of the final volume of Water for Injections at 65° C. After cooling to below 25° C. the Sodium Chloride was added and dissolved followed by the APP. The injection was diluted to volume, sterilised and filled into vials as in Example 2.

An analogous formulation was prepared wherein the APP was replaced by BPP.

EXAMPLE 4

Freeze-dried injection of APP 50 μg/vial

| APP | 2.5mg |
| --- | --- |
| Mannitol | 1.0g |
| Dilute Hydrochloric Acid | sufficient to produce pH 3.0-4.0 |
| Water for Injections B.P. | to 100.0ml |

The APP and Mannitol were dissolved in 9/10 of the final volume of Water for Injections and the pH of the solution adjusted to 3.0-4.0 before diluting to volume. The solution was sterilised by passage through a membrane filter 0.22 μm pore size and distributed aseptically into vials, 2.0 ml/vial. Under aseptic conditions the vials were freeze-dried. At the end of this process the vials were filled with dry sterile Nitrogen and sealed.

The injection is reconstituted before use by the addition of a suitable volume of sterile diluent such as Water for Injections or Physiological Saline Solution.

An analogous formulation was prepared wherein the APP was replaced by BPP.

EXAMPLE 5

APP (*Endocrinology* 83, 1323 (1968)) (1 μg) in water (0.1 ml) was administered by intraperitoneal injection 3 times a day for 25 days to each of 5 male mice (age 6 weeks, weight 23 g) of the NZO strain (genetically obese, hyperglycaemic and hyperinsulinaemic). 5 Matched control animals each received plain water (0.1 ml) by the same route and according to the same schedule. The blood glucose and serum insulin levels were measured at the start and during the course of the experiment and the mean results for the APP-treated group are shown in Table 1. No change in these levels from the values on day 0, which were the same as in the treated group, occurred in the control group over the course of the experiment.

TABLE I

| Day | Blood glucose (mg. %) | Serum Insulin (μU/ml)* |
| --- | --- | --- |
| 0 | 175 | 189 |
| 5 | 162 | |
| 10 | | 99 |
| 15 | 154 | |
| 20 | | 47 |
| 25 | 136 | |

*Beef equivalent.

I claim:

1. A method of treating a mammal for hyperinsulinaemia comprising the parenteral administration to the mammal suffering from hyperinsulinaemia of a non-toxic hyperinsulinaemia treatment effective amount of a polypeptide designated Pancreatic Hormone III or a pharmaceutically acceptable salt or metal complex of said polypeptide.

2. The method of claim 1 wherein said mammal is man.

3. The method of claim 1 wherein said polypeptide is derived from the pancreas of pig, ox or a bird.

4. The method of claim 1 wherein said polypeptide is derived from the pancreas of an ox.

5. A method of treating a mammal for hyperinsulinaemia comprising the parenteral administration to the mammal suffering from hyperinsulinaemia of a nontoxic hyperinsulinaemia treatment effective amount of a polypeptide wherein said polypeptide has the structure:

```
Ala.Pro.Leu.Glu.Pro.Gln.Tyr.Pro.Gly.Asp.Asp.Ala.
 1                  6                       12
Thr.Pro.Glu.Met.Ala.Gln.Tyr.Ala.Ala.Gtu.Leu.
 13             18                      24
Arg.Arg.Tyr.Ile.Asn.Met.Leu.Thr.Arg.Pro.Arg.TyrNH2
```

| 25 | 30 | 36 |
|----|----|----|

6. The method of claim 1 wherein the polypeptide is administered as the free polypeptide.

7. The method of claim 1 wherein the polypeptide is administered as an aqueous solution.

8. The method of claim 1 wherein the polypeptide is administered in an amount of from 0.01 to 100.0 microgram per kilogram body weight of the animal to be treated.

9. The method of claim 1 wherein said polypeptide is administered subcutaneously.

* * * * *